(12) United States Patent
Graf

(10) Patent No.: US 11,172,920 B2
(45) Date of Patent: Nov. 16, 2021

(54) SURGICAL METHODS FOR THE TREATMENT OF PLANTAR PLATE INJURY

(71) Applicant: SportWelding GmbH, Schlieren (CH)

(72) Inventor: Urs Graf, Zürich (CH)

(73) Assignee: SPORTWELDING GMBH, Schlieren (CH)

( * ) Notice: Subject to any disclaimer, the term of this patent is extended or adjusted under 35 U.S.C. 154(b) by 191 days.

(21) Appl. No.: 16/139,267

(22) Filed: Sep. 24, 2018

(65) Prior Publication Data

US 2020/0093477 A1 Mar. 26, 2020

(51) Int. Cl.
*A61B 17/04* (2006.01)
*A61B 17/88* (2006.01)
*A61F 2/08* (2006.01)
*A61B 17/68* (2006.01)
*A61F 2/42* (2006.01)

(52) U.S. Cl.
CPC .......... *A61B 17/0401* (2013.01); *A61B 17/68* (2013.01); *A61B 17/8861* (2013.01); *A61B 17/8869* (2013.01); *A61F 2/0811* (2013.01); *A61B 17/0483* (2013.01); *A61F 2002/0817* (2013.01); *A61F 2002/0847* (2013.01); *A61F 2002/4233* (2013.01)

(58) Field of Classification Search
CPC ............ A61B 17/0401; A61B 17/8861; A61B 17/8869; A61B 17/8872; A61F 2/0811; A61F 2002/0835; A61F 2002/0888
See application file for complete search history.

(56) References Cited

U.S. PATENT DOCUMENTS

| | | | | |
|---|---|---|---|---|
| 9,060,763 | B2 * | 6/2015 | Sengun | A61B 17/0401 |
| 2009/0062854 | A1 * | 3/2009 | Kaiser | A61B 17/0401 606/232 |
| 2009/0306776 | A1 * | 12/2009 | Murray | A61L 17/12 623/13.12 |
| 2012/0197296 | A1 * | 8/2012 | Mayer | A61B 17/0401 606/232 |
| 2013/0023988 | A1 * | 1/2013 | Sinnott | A61B 17/0469 623/13.14 |
| 2013/0178938 | A1 * | 7/2013 | Fallin | A61B 17/0483 623/13.14 |
| 2013/0184818 | A1 * | 7/2013 | Coughlin | A61B 90/06 623/13.14 |

(Continued)

FOREIGN PATENT DOCUMENTS

WO 2017/138917 8/2017

OTHER PUBLICATIONS

Xiao Huang et al., "Novel Porous Hydroxyapatite Prepared by Combining H2O2 Foaming with PU Sponge and Modified with PLGA and Bioactive Glass", Journal of Biomaterials Applications, Apr. 23, 2007, vol. 21, pp. 351-374, http:/jba.sagepub.com/.

(Continued)

*Primary Examiner* — Matthew J Lawson
(74) *Attorney, Agent, or Firm* — Rankin, Hill & Clark LLP

(57) ABSTRACT

A method for the treatment of plantar plate injury including insertion of at least one suture anchor into a bone opening and anchoring the at least one suture anchor and thereafter threading two ends of a suture of at least one anchored suture anchor through the plantar plate and pulling the plantar plate to the bone with the opening and fix the soft tissue to that bone by tying a knot in the suture.

11 Claims, 3 Drawing Sheets

(56) References Cited

U.S. PATENT DOCUMENTS

| | | | | |
|---|---|---|---|---|
| 2014/0094911 A1* | 4/2014 | Fallin | .................... | A61F 2/0805 |
| | | | | 623/13.14 |
| 2017/0143551 A1* | 5/2017 | Coleman | ................ | A61B 17/00 |
| 2017/0156717 A1* | 6/2017 | Triplett | ................ | A61F 2/0811 |
| 2017/0224362 A1* | 8/2017 | Hollis | ................ | A61B 17/8861 |
| 2017/0333101 A1* | 11/2017 | Zeetser | ................ | A61B 17/842 |
| 2019/0282246 A1* | 9/2019 | Windram | ........... | A61B 17/1714 |

OTHER PUBLICATIONS

C.A. Bailey et al., "Biomechanical Evaluation of a New Composite Bioresorbable Screw", The Journal of Hand Surgery, Apr. 2006, vol. 31B, No. 2, pp. 208-212.

S.M. Rea et al., "Bioactivity of ceramic-polymer composites with varied composition and surface topography", Journal of Materials Science; Materials in Medicine, (2004), vol. 15, pp. 997-1005, Cambridge, UK.

Liming Fang et al., "Processing and mechanical properties of HA/UHMWPE nanocomposites", Biomaterials (2006), vol. 27, pp. 3701-3707, Elsevier Ltd.

* cited by examiner

SURGICAL METHODS FOR THE TREATMENT OF PLANTAR PLATE INJURY

BACKGROUND OF THE INVENTION

Field of the Invention

The invention is in the field of surgical procedures and concerns in particular methods for the treatment of plantar plate injury. The inventive methods refers mainly to the repair of severe injuries, where the plantar plate is pulled off the bone or correction of hammer toes and involves using of bone anchor to secure the ligament to the bone.

Description of Related Art

The plantar plate is a fibro-cartilaginous ligament on the underside (plantar) of the foot, running along the first joint of each toe. Its purpose is to protect the head of the metatarsal from pressure and injury and to prevent the over extension of the toe by hindering the joint from bending upward beyond the normal range of motion. It also keeps each toe stabilized to prevent them from drifting out of their normal alignment. The plantar plate is also called the volar plate, volar ligament, or plantar ligament. A plantar plate injury refers to damage to the strong supporting ligament of a toe. Injury to the plantar plate is usually caused by overuse, such as from running; obesity; or wearing high heeled shoes too often. Damage to the plantar plate can be chronic and include a lengthening or partial tear of the ligament. The most serious form of plantar plate injury is a total rupture of the plate, when the ligament tears completely and leaves no link between the metatarsals and phalanges. Severe damage to the Plantar Plate is frequent in professional sports. Most commonly the 2nd toe is involved, but any toe can be damaged. A chronic plantar plate injury is very different than an acute injury. Here the plantar plate (ligament) will have micro-tears and stretch out over time. A chronic injury can occur from a trauma where the initial plantar plate tear was undiagnosed—this is best considered a non-healing injury. Alternatively, a chronic injury of the plantar plate may occur from biomechanical imbalance to the foot. Chronic plantar plate injury can develop into a hammer toe (toe contracture). Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery may be required to correct the deformity. A turf toe injury refers to hyperextension injury to the hallux metatarsophalangeal (MTP) joint which may include a complete rupture of the plantar structures of the hallux MTP joint.

To fix this problem, surgeons have historically transferred tendons from the bottom of the toe to the top of the toe to pull the toe back down to the floor. The 'flexor to extensor tendon transfer' is still considered a very good operation and is still used today. An alternative to the flexor-extensor tendon transfer is to directly repair the plantar plate. Surgical procedure for a plantar plate repair can be done either from a plantar or dorsal approach. The dorsal approach has been found to include many advantages over the plantar approach, especially in that a patient can bear weight on the foot after about 48 hours of surgery and that the correction tends to be solid. The dorsal approach can reduce the risk of compromising the principal blood supply to the affected digits and with the plantar approach the level of complications, such as scar formation is greater than with the dorsal approach. In addition, if an osteotomy is necessary, the dorsal approach enables the surgeon to repair the plantar plate and the collateral ligaments and conduct osteotomy through the same incision. The repair is performed with sutures to re-approximate or advance the plantar plate back to the base of the toe. Part of the operation may involve shortening the toe a few millimeters with a 'Weil Osteotomy.' Shortening the toe allows the surgeon to gain access to the plantar plate and also decreases tension and forefoot pressure post-operatively.

Employing a dorsal approach and combining Weil's osteotomy is well known in the art and usually includes a number of steps including: performing a Weil's osteotomy allowing the capital fragment to be recessed under the metatarsal; digital distraction by a distraction clamp over K-wires; assessing the plantar plate and repairing same by passing a suture through the plantar plate; followed by the step of repairing the plantar plate back to the proximal phalanx. The success of this procedure depends greatly on the ability to place the suture in the plantar plate correctly. This often proves fairly difficult because the dorsal approach results in soft tissue limitations meaning the space is confined. The confined space further necessitates retraction of soft tissue. A plethora of methods and tools have been developed to facilitate the placing of this suture in a convenient and accurate manner. The most common is by employing the various devices described in US 2013/0184818.

Current systems such as the one described in WO 2017/138917 A1 require at least one tunnel or through bore to be drilled into the phalangeal bone of the treated joint in order to achieve fixation of the plantar plate. The suture strands need to get through the tunnels, which is difficult to handle and often requires the operation site to be opened wide to allow access. The creation of bone tunnels is relatively complicated, often requiring an extensive exposure to identify the margins of the tunnels. That process is time-consuming and fraught with complications, which include poor tunnel placement and fracture of the overlying bone bridge.

The creation of bone tunnels is relatively complicated, often requiring an extensive exposure to identify the margins of the tunnels. The process is time-consuming and fraught with complications, which include poor tunnel placement and fracture of the overlying bone bridge. After creation of tunnels, sutures must be passed through the tunnels. Finally, the procedure can be compromised if the bone bridge above the tunnel breaks, resulting in loss of fixation. A brittle bone may not last when tying a suture after passing the bone tunnel.

SUMMARY OF THE INVENTION

It is accordingly an object of the present invention to provide a plantar plate repair method with which the above disadvantages could at least partially be overcome or alleviated and/or to provide a more useful alternative to the known methods. In particular, it is an object to provide a method for the treatment of plantar plate injury without using transosseous tunnels.

The invention provides surgical method for the treatment of plantar plate injury and techniques for complete plantar plate repair. The present invention refers to methods for reconstruction of the plantar plate through a dorsal, lateral or medial incision, restoring the normal alignment of the metatarsophalangeal joint. A medial access is possible in case of the big toe and a lateral access in case of the little toe.

Thereby healing complications should be minimized, e.g. by minimizing trauma to the bone and the surrounding tissue. The method for the treatment of plantar plate injury according to the present invention includes the steps of: i) performing a longitudinal dorsal, lateral or medial incision to expose a metatarsophalangeal joint, ii) distracting the metatarsophalangeal joint to expose a plantar plate, iii) inserting at least one suture anchor into a bone opening and anchoring the at least one suture anchor, iv) threading two ends of a suture of at least one anchored suture anchor through the plantar plate, and v) pulling the plantar plate to the bone with the opening and fix the soft tissue to that bone by tying a knot in the suture.

One main difference of the present invention refers to the sequence of the steps used. So far it is necessary to thread the suture through the plantar plate and the bone tunnel and subsequently set the anchor or place the implant for fixation of the suture. With the present invention it is possible to set the anchor firstly and secondly thread the suture of the anchored anchor through the plantar plate and pull it to the bone. Therefore it is possible to insert a suture anchor with previously attached sutures.

Using the methods of the invention it is for the first time possible during plantar plate repair to lock the suture to the bone, with the free end(s) of the suture extending out of the bone, before the suture is (are) passed through the plantar plate. Therefore one aspect of the present invention refers to methods for treatment of plantar plate injury according to the present invention including the steps of: i) performing a longitudinal dorsal, lateral or medial incision to expose a metatarsophalangeal joint, ii) hereafter distracting the metatarsophalangeal joint to expose a plantar plate, iii) subsequently inserting at least one suture anchor into a bone opening and anchoring the at least one suture anchor, iv) after this threading two ends of a suture of at least one anchored suture anchor through the plantar plate, and v) hereafter pulling the plantar plate to the bone with the opening and fix the soft tissue to that bone by tying a knot in the suture.

Another advantage of the method of the present invention is that the two ends of the suture may be passed through the plantar plate in a plantar to dorsal direction. Thereafter the sutures are fastened with a knot, which may be any common surgical knot. The knot can be placed between the phalangeal bone and the dorsal side of the plantar plate. The knot may be located below the bone opening. Therefore, the length of the suture is very short. Compared to common techniques the suture is about ten-times shorter. This increases the stiffness of the construct and avoids the so called "bungee effect". It is proposed that a long suture and its elasticity within the bone tunnel causes micro-movements of the reattached plantar plate compromising healing, besides problems like abrasion of the suture in the tunnel. Under load, the "bungee effect" may also allow gaping of the plantar plate off the bone, which could even be a cause of failure.

The method of the present invention is especially suitable for the treatment of a hammer toe or a turf toe as well as a deformity of the proximal interphalangeal joint of the little toe. There are some small differences depending on the toe to be treated. One refers to the incision. The metatarsophalangeal joint of the big toe and the little toe may be exposed using a medial incision or a dual incision for medial and lateral access. Therefore one embodiment of the invention refers to the method wherein the metatarsophalangeal joint is the joint of the second, third or fourth toe. In this case the method includes the step: performing a longitudinal dorsal incision to expose a metatarsophalangeal joint. Another embodiment of the invention refers to the method, wherein the metatarsophalangeal joint is the joint of the big or little toe and comprises: performing a longitudinal medial incision to expose a metatarsophalangeal joint.

For treatment of the metatarsophalangeal joint of the big toe it may be suitable to use two anchors. These anchors are set side by side and dorsal of the articulate surface on the proximal phalanx. Therefore one embodiment of the invention refers to a method wherein the metatarsophalangeal joint is the joint of the big toe and the method comprises: performing a longitudinal medial incision to expose a metatarsophalangeal joint, distracting the metatarsophalangeal joint to expose a plantar plate, inserting at least two suture anchors into a bone opening and anchoring the at least one suture anchor, threading two ends of a suture of each anchored suture anchor through the plantar plate, pulling the plantar plate to the bone with the opening and fix the soft tissue to that bone by tying a knot in the suture.

It is possible to use a wide range of known suture anchors within the method of the invention. The suture anchor should be rather small and holding one suture with two open ends. Nevertheless, it is advantageously the at least one suture anchor used within the method of the present invention includes a material having thermoplastic properties. The suture anchor having thermoplastic properties may be anchored in the bone opening with the aid of vibratory energy used for in situ liquefaction of the material having thermoplastic properties.

A suture anchor is a small device used during surgical procedures to attach soft tissue, such as ligaments and tendons, to bone. This may be achieved by tying one end of a suture to soft tissue and the other end to a device which "anchors" the suture to the bone. Suture anchors typically are implanted into the bone with suture attached to the anchor. Various techniques of suture attachment have been developed. Most commonly a suture anchor includes an elongate body to which a suture has been attached using an eyelet or the like. Thereby the eyelet—is a hole or a loop in the anchor to through which the suture passes. Suture anchors may be made of titanium metal, polyetheretherketone thermoplastic, or biodegradable absorbable material. There are many suture anchors on the market today. In general, they can be classified as screw-in or and non-screw-in anchors, commonly using an interference fit. A suture is typically an elongate flexible filament, but may take a variety as different thread or thread-like structures, including without limitation fibers, lines, and the like. A suture may be a homogeneous or heterogeneous, and may also include a single filament or a composite suture, such as a two or more twisted or woven filaments. In addition, a suture may be made from a wide array of absorbable (i.e., metabolized by the body) or non-absorbable materials known in the art.

Materials having thermoplastic properties suitable for the suture anchor used in the method according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

One embodiment of the present invention refers to the method for the treatment of plantar plate injury according to the present invention, wherein the at least one anchor is fully made of a bio-degradable material. Specific embodiments of bio-degradable materials are Polylactides like LR706 PLD-LLA 70/30, R208 PLDLA 50/50, L210S, and PLLA 100% L, all of Bohringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are Polyetherketone (PEEK Optima, Grades 450 and 150, Invibio Ltd), Polyetherimide, Polyamide 12, Polyamidell, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 ff. (PE, Hostalen Gur 812, Hochst AG), pages 164 ff. (PET) 169ff (PA, namely PA 6 and PA 66), 171 ff. (PTFE), 173 ff. (PMMA), 180 (PUR, see table), 186 ff. (PEEK), 189 ff. (PSU), 191 ff (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseointegration stimulating fillers that are only partially or hardly degradable, for non-degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), J A Juhasz et al. Biomaterials, 2004 March; 25(6):949-55. Particulate filler types include: coarse type: 5-20 μm (contents, entially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone.

The suture anchor used in the method according to the invention may consist of any suitable material or material combination (e.g. polymer, metal, ceramic, glass) which material may be bio-resorbable or not bio-resorbable and liquefiable or not liquefiable. Non-bioresorbable or non-biodegradable such materials may include surfaces equipped for furthering osseointegration (e.g. per se known surface structures or coatings) where in contact with the bone tissue, in particular if the material of the suture anchor is bio-resorbable or bio-degradable and therefore the anchoring function needs to be gradually taken over by osseointegration. Good results have, e.g., been achieved with suture anchors of polylactic acid (PLA) filled with Hydroxyapatite or calciumphosphates, in particular of PLLA filled with 60% tricalciumphosphate or PDLLA 70%/30% (70% L and 30% D/L) filled with 30% biphasic calciumphosphate, combined with suture anchors of PLDLLA 70%/30% (70% L and 30% D/L), as available from Bohringer as LR706. In the case of the suture anchor being integrated in the suture anchor, the two items may consist of the same material, e.g. the above named PLLA filled with 60% tricalciumphosphate or PDLLA 70%/30% (70% L and 30% D/L) filled with 30% biphasic calciumphosphate, wherein the filler content may be smaller in areas in which the material is to be liquefied than in other areas.

If the suture anchor is to be forced into the hard tissue, it needs to include at least in its distal end a material having a corresponding mechanical strength, which is dependent on the mechanical resistance expected of the hard tissue into which the anchor is to be forced. If such resistance is relatively high (forcing through cortical bone or hard and dense cancellous bone) the distal end of the anchor includes e.g., a metal such as, e.g., titanium or a titanium alloy, a ceramic material such as, e.g., sintered calcium phosphate (e.g., hydroxyapatite) or engineering ceramics (e.g. zirkonia, alumina) or PEEK or a comparable high temperature resistant polymer, while other anchor portions are made e.g. of a biocomposite material such as, e.g., the above mentioned filled polylactides or of one of the other above mentioned thermoplastic polymers. Alternatively such distal end of the anchor may include a hard and possibly abrasive coating, e.g., made by plasma sprayed deposition of calcium phosphate or titanium powder on PEEK or polylactide or biocomposites.

The energy used for the liquefaction of the material having thermoplastic properties is preferably mechanical vibration, in particular ultrasonic vibration generated by a vibration source (e.g. piezoelectric vibration generator possibly including a booster to which the tool is coupled) and the anchoring tool is suitable for transmission of the vibration from its proximal end to its distal face, preferably such that the distal face vibrates with a maximal longitudinal amplitude. For the in situ liquefaction the vibration is transmitted from the distal tool face to the suture anchor and transformed into friction heat in places where the suture anchor is held against a counter element (hard tissue and/or part of the suture anchor). It is possible also to activate the anchoring tool to vibrate in a radial or in a rotational direction.

Alternatively, the energy source may be a laser, preferably emitting laser light in the visible or infrared frequency range and the anchoring tool is equipped for transmitting this light to its distal end, preferably via glass fiber. For the in situ liquefaction the laser light is transmitted into the suture anchor and absorbed where liquefaction is desired, wherein the material of the suture anchor may contain particles or substances effecting such absorption.

As anchoring of the suture anchor is only little dependent on the quality of the hard tissue, the method according to the invention is suitable in particular for fixating a suture anchor in hard tissue of an only small mechanical stability, wherein this is largely true even if the first fixating step is chosen to result in only a very weak fixation in such hard tissue.

In one aspect of the invention, a method for plantar plate repair includes exposing a metatarsophalangeal joint, wherein the metatarsophalangeal joint includes a metatarsal, a proximal phalanx, a plantar plate, and a flexor tendon; detaching a plantar plate from the proximal phalanx and the flexor tendon; distracting the metatarsophalangeal joint; forming one bone opening in the proximal phalanx; providing a suture anchor and anchoring the suture anchor in the bone opening; threading two free suture ends of the suture anchor through a distal portion of the plantar plate; advancing the plantar plate until it rests against the proximal phalanx; reposition of the proximal phalanx; tensioning the suture; tying a knot in the suture, the knot resting against the dorsal side of the plantar plate; and closing the exposure of the metatarsophalangeal joint.

One embodiment refers to a method for the treatment of plantar plate injury according to the present invention, wherein threading two ends of a suture through the plantar plate includes passing the suture in a plantar to dorsal direction. Another embodiment refers to a method for the treatment of plantar plate injury according to the present invention, wherein tying a knot in the suture includes tying the knot near a plantar phalangeal cortex of the phalangeal bone resting against the dorsal side of the plantar plate. It is therefore possible that the knot is placed outside the articular surface. Therefore the impingement risk is minimized.

When threading the ends of a suture through the plantar plate one can use a suture passing instrument such as a Mini Scorpion DX™. The suture passes from the anchor to the adjoining plantar plate only (see FIG. 4), thus it is very short. One advantage of the present method is the very short suture, which provides great tensile strength as well as stiffness and therefore allows only little play.

The bone opening formed in the proximal phalanx may be a blind hole. The bone opening or blind hole can be placed outside the articular surface, respectively outside the metatarsophalangeal joint or only at the periphery of the articular surface. The bone opening may be placed adjoining to the plantar plate insertion. In more detail it may be placed proximal to the insertion side but outside the articular surface. In other words the bone opening may be placed within the curvature (proximal extremities) of the proximal phalanx. Consequently, it is possible that the at least one anchor is placed outside the articulating sliding surfaces.

The bone opening should form an angle with the tangent running through the plantar plate insertion side of 30 to 60°.

The inventive method avoids transosseous holes and is thus, less invasive. It is possible to maintain greater bone strength versus systems that use multiple bone tunnels. Furthermore to pass a suture through a bone tunnel and retrieval of the suture at or very near the plantar plate, can be very tedious and time consuming in the operating room. Within the present invention the suture anchor can easily be placed by exposing the joint and allows for a smaller incision. In addition, the bone tunnel is not completely filled with the suture and there is a space left in the bone tunnel. A space remaining in a bone tunnel causes the following subcutaneous hemorrhage, pain, and swelling due to bleeding from bone marrow in a bone tunnel, and therefore the risk of infection increases. Compared with common surgical methods for repairing plantar plate injury the inventive method causes less trauma.

Inserting at least one suture anchor into a bone opening and anchoring the at least one suture anchor may include the following steps: Introducing the suture anchor into the bone opening with the suture having two freely accessible ends by pushing the suture anchor into the bone opening using a tool and by simultaneously or later transmitting energy via the tool to the suture anchor thereby liquefying material of the suture anchor having thermoplastic properties.

Using the inventive method there is no need to pull the anchor tight to determine whether full insertion has been reached. One embodiment refers to a method for the treatment of plantar plate injury according to the present invention, wherein there is no need to pull the at least one anchor tight.

The method according to the invention may include creating a Weil osteotomy of a distal epiphysis of the metatarsal; temporarily fixing a distal capital fragment of the metatarsal to a plantar aspect of the distal epiphysis of the metatarsal; removing the temporary fixation of the distal capital fragment of the metatarsal to the distal epiphysis of the metatarsal; reducing the distal capital fragment of the metatarsal against the distal epiphysis of the metatarsal; and securing the distal capital fragment of the metatarsal to the distal epiphysis of the metatarsal. Therefore one aspect of the present invention refers to a method for the treatment of plantar plate injury including a Weil osteotomy of a distal epiphysis of the metatarsal of the exposed metatarsophalangeal joint.

DETAILED DESCRIPTION OF THE INVENTION

The following more detailed description of the embodiments of the method is a representative of exemplary embodiments of the technology, wherein similar parts are designated by same numerals throughout. Standard medical planes of reference and descriptive terminology are employed in this specification. A sagittal plane divides a body into right and left portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Proximal means toward the trunk, or, in the case of an inanimate object, toward a user. Distal means away from the trunk, or, in the case of an inanimate object, away from a user. Dorsal means toward the top of the foot. Plantar means toward the sole of the foot. Ipsilateral means on the same side of the body. Contralateral means on the opposite side of the body.

Figure 1:
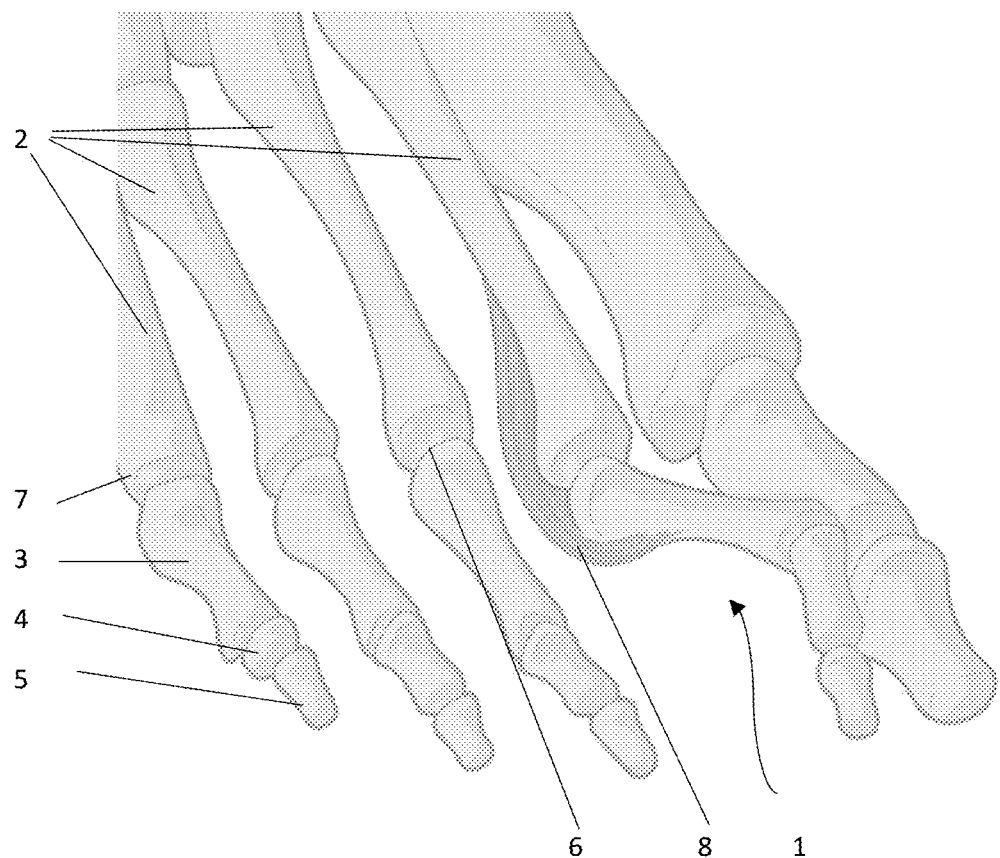
FIG. 1 shows a schematical overview of the foot with a hammer toe or contracted toe as a deformity of the proximal interphalangeal joint of the second toe causing it to be permanently bent.
Figure 2:
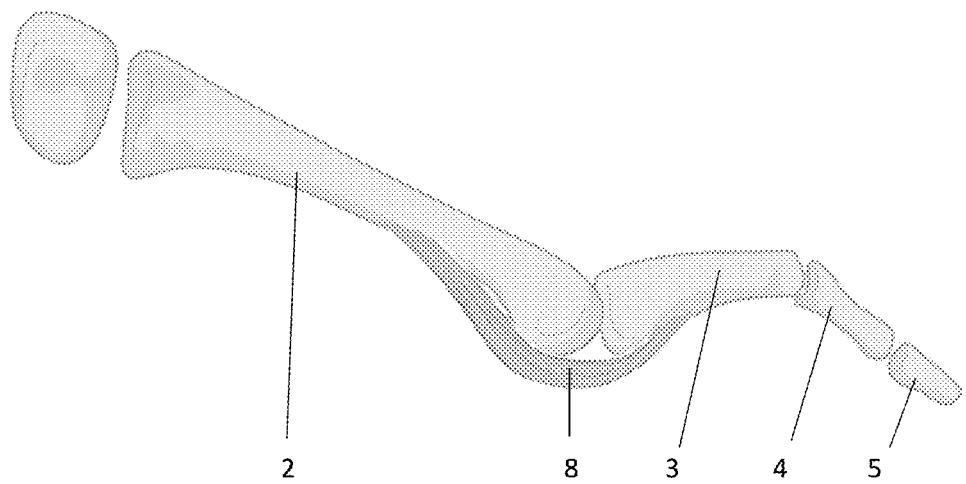
FIG. 2 shows side view of a deformed proximal interphalangeal joint of the second toe causing it to be permanently bent.

FIGS. 1 and 2 illustrate the most important anatomical structures of a foot with a hammer toe (1) or contracted toe as deformity of the metatarsophalangeal joint (6) of the second toe causing it to be permanently bent. The metatarsophalangeal joints (6) are the joints between the metatarsal bones (2) of the foot and the proximal phalanges (3) of the toes. The great toe only has two phalanx bones (proximal and distal phalanges) and only one interphalangeal joint, which is often abbreviated as the "IP joint." The rest of the toes each have three phalanx bones, the proximal (3), middle (4), and distal phalanges (5), so they have two interphalangeal joints. The plantar plate (8) is a rectangular, fibrocartilaginous structure overlying plantar aspects of metatarsophalangeal joints and is formed from distal parts of plantar aponeurosis and plantar aspects of metatarsophalangeal joint capsules.

Figure 3:
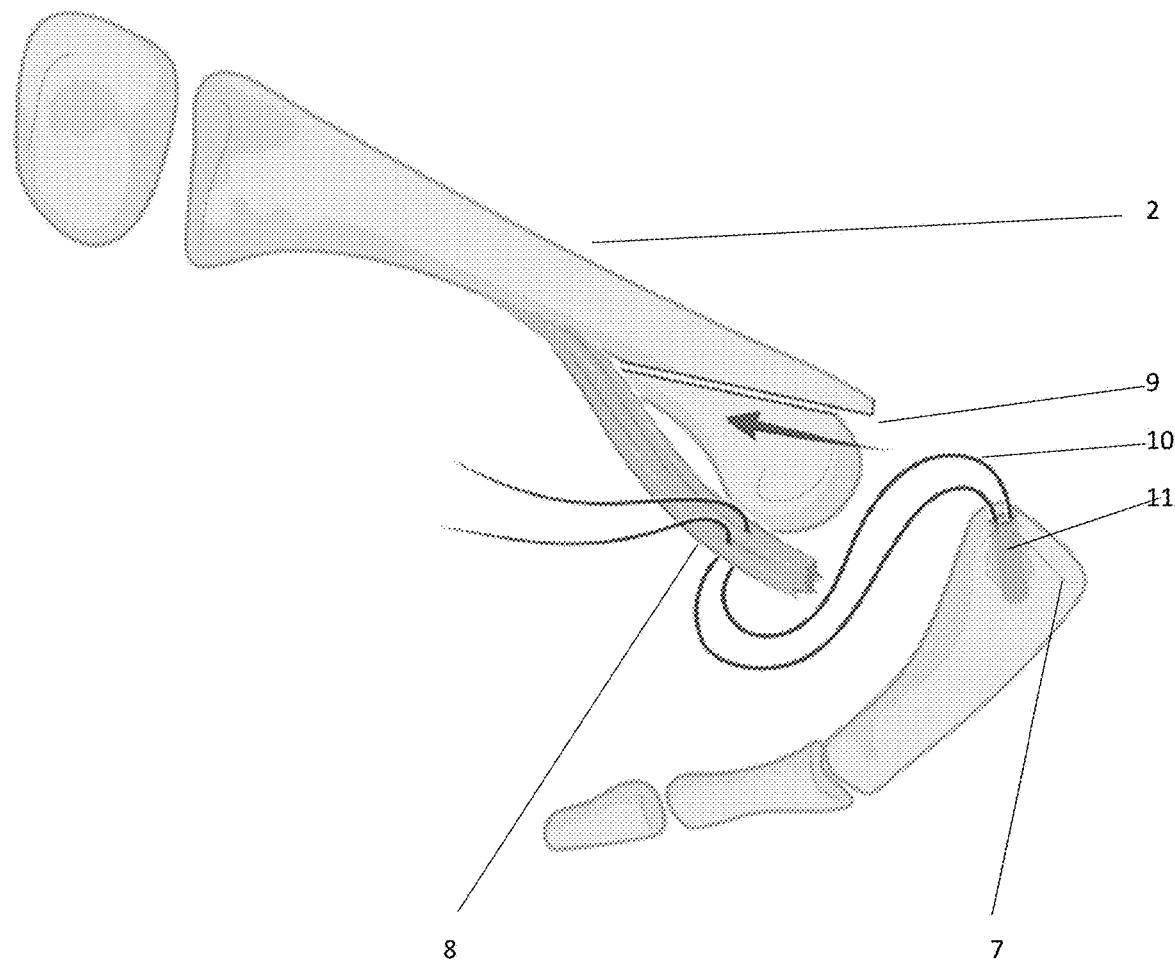
FIG. 3 shows first steps of the method according to the invention including insertion and anchoring of a suture anchor and threading two ends of a suture of through the plantar plate.
Figure 4:
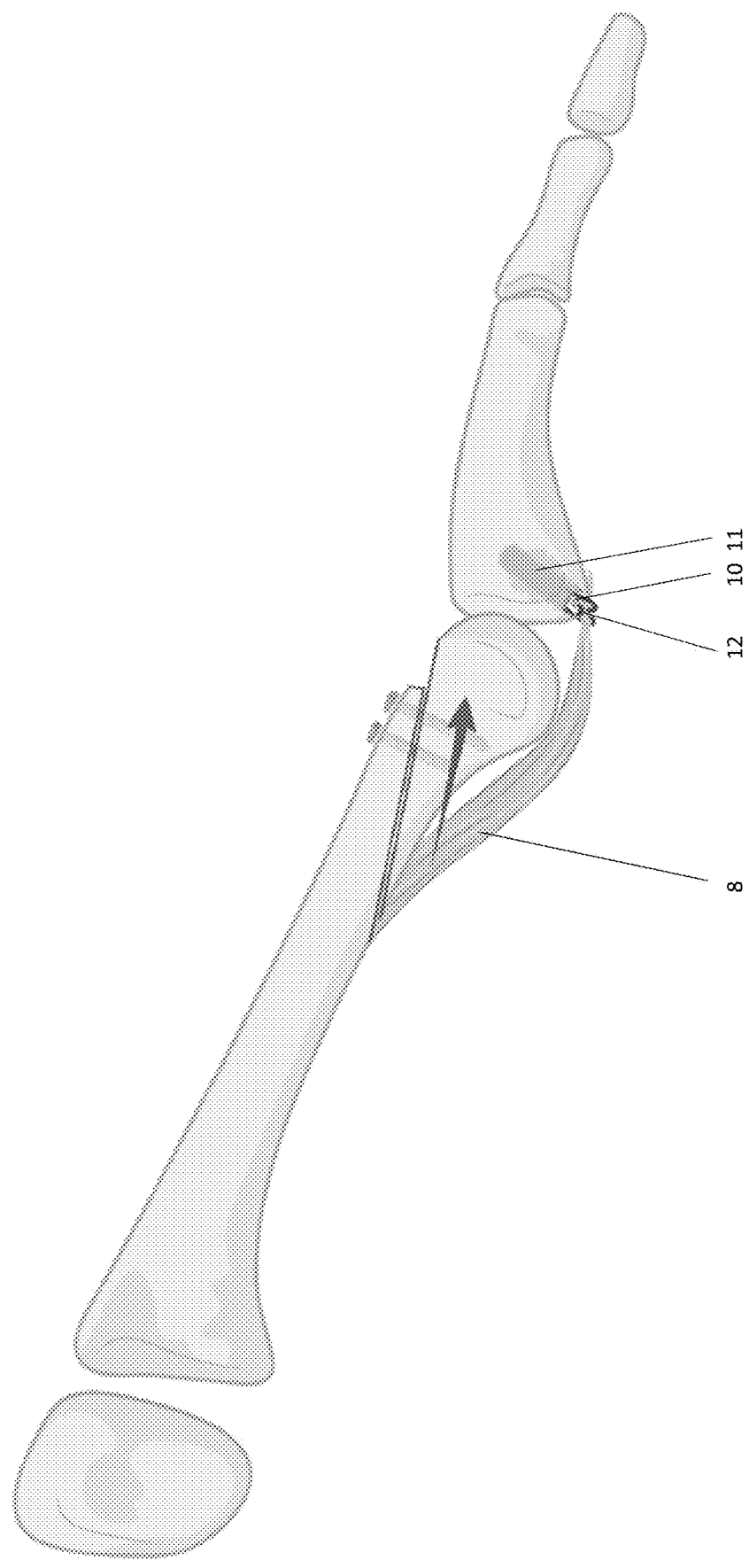
FIG. 4 shows additional steps of the method according to the invention including repositioning the metatarsal head.

An exemplary method of plantar plate repair employing a dorsal approach and combining a Weil osteotomy in accordance with the present invention is shown in the FIGS. 3 and 4. A dorsal longitudinal incision is centered over the second metatarsophalangeal joint (6). A longitudinal capsulotomy is performed to expose the affected second metatarsophalangeal joint (6). A partial collateral ligament release off of the proximal phalanx (3) of the metatarsophalangeal joint (6) may improve visualization. A metatarsal shortening osteotomy (Weil osteotomy, 9) is performed using a sagittal saw. The saw cut is made parallel to the plantar aspect of the foot. The capital fragment is provisionally pushed proximally and may be fixed with a temporary vertical Kirschner wire (k-wire), to hold it in a retracted position. A plantar plate distractor may be placed and spread to expose the plantar plate (8). The most common tear patterns of the plantar plate are partial and complete distal transverse tears at the distal insertion of the plantar plate. In case of partial transverse tear on should make the partial tear a complete tear as close as possible to the insertion of the plantar plate to the proximal phalanx (3). This reflects the plantar plate off the flexor tendon sheath.

A blind hole is created dorsal of the articulate surface on the proximal phalanx (plantar rim of the proximal phalanx). Thereafter a suture anchor (11) is inserted in the blind hole and anchored in a way that two free ends of the suture are accessible.

The distal plantar plate (8) is transfixed proximal to the transverse tear using, for example, a small curved needle or a suture passing instrument to pass the two free ends of the suture (10) through the plantar plate (8). As shown in FIG. 3 passing the suture (10) through the plantar plate occurs preferably, plantar to dorsal. When passed through the plantar plate, the suture tis pulled tight, thereby advancing the plantar plate onto the proximal phalanx (3). The suture (10) is then tied between the plantar plate (8) and the proximal phalanx (3). After removal of the joint distractor the phalanx is plantar flexed.

The distal plantar edge of the proximal phalanx may be roughened with a burr or curette to prepare a surface for re-implantation of the plantar plate. The metatarsal shortening (Weil) osteotomy (9) is moved to anatomic positioning, typically with 1-2 mm of shortening at the osteotomy site. It is fixed in optimal position with one or two small screws or k-wire. Wound closure is performed.

The inventor used the inventive method to treat some patients successfully. The fact that the suture does not have to be passed through bone tunnels meant considerable time savings around 15 to 20 minutes less per operation. In addition, he could observe that for the patients this new method involves less swelling and pain. This causes better and faster wound healing for all patients treated so far.

In addition it is suitable to use very small anchors such as the SportWelding® Fiji Anchor®. This together with the short suture and the less traumatic approach enable to treat also plantar plate injuries of the third to fifth toe using the methods of the present invention.

What is claimed is:

1. A method for the treatment of plantar plate injury comprising the following steps:
   i) performing a longitudinal dorsal, lateral or medial incision to expose a metatarsophalangeal joint,
   ii) after step i), distracting the metatarsophalangeal joint to expose a plantar plate,
   iii) after step ii), inserting at least one suture anchor into a bone opening being a blind hole and anchoring the at least one suture anchor,
   iv) after step iii), threading two ends of a suture of at least one anchored suture anchor through the plantar plate,
   v) after step iv) or at least partially in parallel with step iv), pulling the plantar plate to the bone with the opening, and fixing the soft tissue to that bone by tying a knot in the suture between the phalangeal bone and the dorsal side of the plantar plate;
   wherein the at least one suture anchor comprises a material having thermoplastic properties and is anchored in the bone opening with the aid of vibratory energy used for in situ liquefaction of the material having thermoplastic properties.

2. The method according to claim 1, wherein threading two ends of a suture through the plantar plate includes passing the suture through the plantar plate in a plantar to dorsal direction.

3. The method according to claim 1, wherein the metatarsophalangeal joint is the joint of the second, third or fourth toe and the method comprises: performing a longitudinal dorsal incision to expose a metatarsophalangeal joint.

4. The method according to claim 1, wherein the metatarsophalangeal joint is the joint of the big or little toe and the method comprises: performing a longitudinal, lateral or medial incision to expose a metatarsophalangeal joint.

5. The method according to claim 1, wherein there is no need to pull the at least one anchor tight.

6. The method according to claim 1, wherein the at least one anchor is fully made of a bio-degradable material.

7. The method according to claim 1, wherein the at least one anchor is placed outside the articular surface.

8. The method according to claim 1, wherein the knot is placed outside the articular surface.

9. The method according to claim 1, comprising a Weil osteotomy of a distal epiphysis of the metatarsal of the exposed metatarsophalangeal joint.

10. The method according to claim 1, wherein the metatarsophalangeal joint is the joint of the big toe and the method comprises:
   performing a longitudinal medial incision to expose a metatarsophalangeal joint,
   distracting the metatarsophalangeal joint to expose a plantar plate,
   inserting at least two suture anchors, each into a separate bone opening and anchoring the at least two suture anchors, wherein the at least two suture anchors include the at least one suture anchor,
   threading two ends of a suture of each anchored suture anchor through the plantar plate,
   pulling the plantar plate to the bone with the opening and fix the soft tissue to that bone by tying a knot in the suture.

11. The method according to claim 1, wherein the suture is attached to the at least one anchored suture anchor before step iv) is carried out.

* * * * *